(12) United States Patent
Barry

(10) Patent No.: US 7,776,072 B2
(45) Date of Patent: Aug. 17, 2010

(54) SYSTEM AND METHOD FOR ALIGNING VERTEBRAE IN THE AMELIORATION OF ABERRANT SPINAL COLUMN DEVIATION CONDITIONS

(76) Inventor: Mark A. Barry, 2800 E. Desert Inn Rd. #100, Las Vegas, NV (US) 89121

( * ) Notice: Subject to any disclaimer, the term of this patent is extended or adjusted under 35 U.S.C. 154(b) by 544 days.

(21) Appl. No.: 11/202,409

(22) Filed: Aug. 10, 2005

(65) Prior Publication Data
US 2006/0195092 A1  Aug. 31, 2006

Related U.S. Application Data

(63) Continuation-in-part of application No. 11/027,026, filed on Dec. 30, 2004.

(51) Int. Cl.
*A61B 17/70* (2006.01)
(52) U.S. Cl. ........................ 606/265; 606/279
(58) Field of Classification Search ............. 606/60–61, 606/104, 264, 279, 265, 102
See application file for complete search history.

(56) References Cited

U.S. PATENT DOCUMENTS

| 5,102,412 | A |   | 4/1992  | Rogozinski |
| 5,112,332 | A |   | 5/1992  | Cozad et al. |
| 5,116,334 | A |   | 5/1992  | Cozad et al. |
| 5,181,917 | A |   | 1/1993  | Rogozinski |
| 5,281,223 | A | * | 1/1994  | Ray ............................ 606/61 |
| 5,306,275 | A |   | 4/1994  | Bryan |
| 5,498,262 | A |   | 3/1996  | Bryan |
| 5,545,166 | A |   | 8/1996  | Howland |
| 5,630,816 | A |   | 5/1997  | Kambin |
| 5,676,665 | A |   | 10/1997 | Bryan |
| 5,704,937 | A | * | 1/1998  | Martin ...................... 606/86 A |
| 5,772,661 | A |   | 6/1998  | Michelson |
| 5,810,817 | A |   | 9/1998  | Roussouly et al. |
| 5,928,232 | A |   | 7/1999  | Howland et al. |
| 5,947,965 | A |   | 9/1999  | Bryan |
| 6,015,409 | A |   | 1/2000  | Jackson |
| 6,090,113 | A | * | 7/2000  | Le Couedic et al. ........... 606/61 |
| 6,267,765 | B1 |  | 7/2001  | Taylor et al. |
| 6,375,657 | B1 |  | 4/2002  | Doubler et al. |
| 6,440,132 | B1 |  | 8/2002  | Davis |
| 6,458,131 | B1 |  | 10/2002 | Ray |
| 6,558,390 | B2 |  | 5/2003  | Cragg |
| 6,652,526 | B1 |  | 11/2003 | Arafiles |

(Continued)

OTHER PUBLICATIONS

U.S. Appl. No. 11/027,026, Mark A. Barry.

(Continued)

*Primary Examiner*—Eduardo C Robert
*Assistant Examiner*—Elana B Fisher
(74) *Attorney, Agent, or Firm*—Patton Boggs LLP

(57) ABSTRACT

A system and method for ameliorating spinal column anomalies, such as scoliosis, includes bone screws which are to be implanted in the pedicle region(s) of individual to-be-derotated vertebrae and in vertebrae to which balancing forces must be applied as the spinal column is manipulated en mass to achieve an over-all correction of the condition. A pedicle screw cluster derotation tool simultaneously engages multiple pedicle screws and transmits manipulative forces to multiple vertebrae to effect a whole-spine correction. Pre-contoured spinal rods are engaged post-derotation to secure the correction.

4 Claims, 5 Drawing Sheets

U.S. PATENT DOCUMENTS

| | | | |
|---|---|---|---|
| 6,743,231 B1 | 6/2004 | Gray et al. | |
| 6,749,614 B2 | 6/2004 | Teitelbaum et al. | |
| 6,802,844 B2 | 10/2004 | Ferree | |
| 6,821,277 B2 | 11/2004 | Teitelbaum | |
| 6,827,719 B2 | 12/2004 | Ralph et al. | |
| 2005/0245928 A1* | 11/2005 | Colleran et al. | 606/61 |
| 2006/0149236 A1* | 7/2006 | Barry | 606/61 |

OTHER PUBLICATIONS

Richard P. Schlenk, M.D., Robert J. Kowalski, M.D., P.E., and Edward C. Benzel, M.D. Biomechanics of spinal deformity, Neurosurg Focus 14 (1);Article 2, 2003.

* cited by examiner

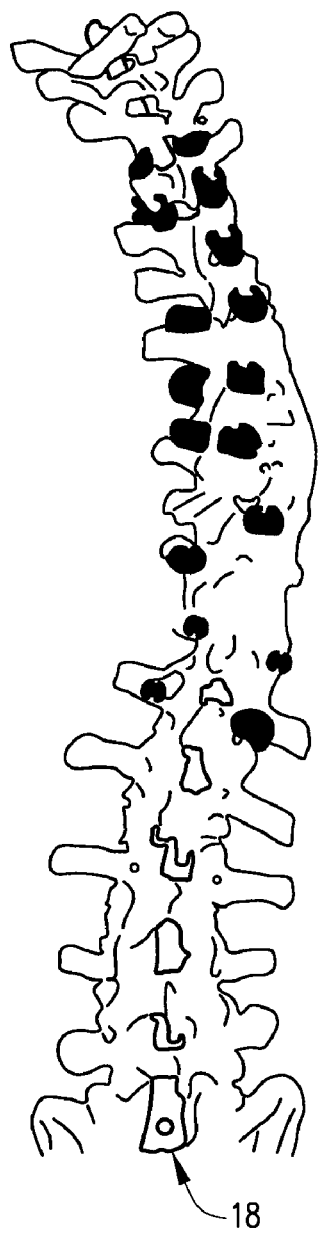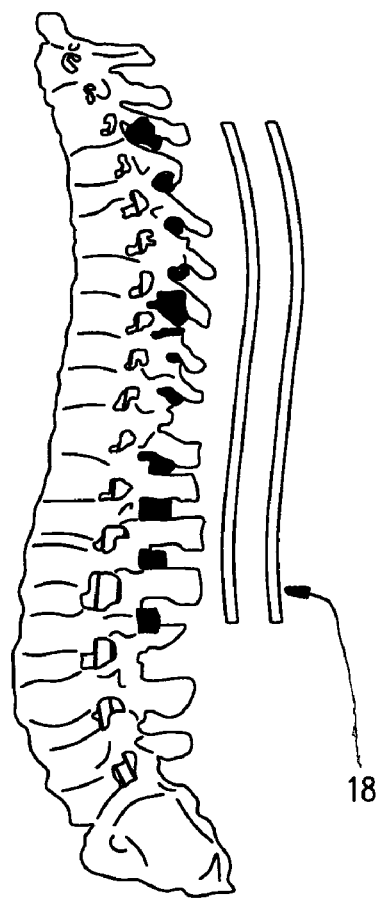
FIG. 2
FIG. 3

SYSTEM AND METHOD FOR ALIGNING VERTEBRAE IN THE AMELIORATION OF ABERRANT SPINAL COLUMN DEVIATION CONDITIONS

PRIORITY CITATION

This Patent application is a Continuation-in-Part Application, the parent application from which priority is claimed being U.S. patent application Ser. No. 11/027,026, filed 30 Dec. 2004.

BACKGROUND OF THE INVENTION

1. Field of the Invention

The present invention relates to methods and apparatus for management and correction of spinal deformities, such as scoliosis.

2. Background Information

A serious deficiency presently exists with respect to conventional treatment and instrumentation for treating spinal deviation anomalies, such as scoliosis.

This circumstance presents a serious medical challenge, because scoliosis, other than mild to moderate cases, is a well-recognized health risk.

If scoliosis curvature exceeds 70 degrees, severe twisting of the spine occurs. This can cause the ribs to press against the lungs, restrict breathing, and reduce oxygen levels. The distortions may also affect the heart and possibly cause dangerous changes.

Eventually, if the curve reaches more than 100 degrees, both the lungs and the heart can be injured. Patients with this degree of severity are susceptible to lung infections and pneumonia. Curves greater than 100 degrees are associated with elevated mortality rates.

A number of factors associated with scoliosis increase the risk for bone loss, which is referred to as osteopenia. People with osteopenia are at greatly increased risk of osteoporosis, a common problem in older women that can cause broken bones and is particularly dangerous for women with a history of scoliosis. Experts recommend that children with scoliosis be screened for osteopenia so that measures can be taken to help prevent osteoporosis later Present treatment regimens for scoliosis carry their own risks and side effects, which include:

Spinal fusion disease. Patients who are surgically treated with fusion techniques lose flexibility and may experience weakness in back muscles due to injuries during surgery.

Disk degeneration and low back pain. With disk degeneration, the disks between the vertebrae may become weakened and may rupture.

Height loss.

Lumbar flatback. This condition is most often the result of a scoliosis surgical procedure called the Harrington technique, used to eliminate lordosis (exaggeration of the inward curve in the lower back). Adult patients with flatback syndrome tend to stoop forward. They may experience fatigue and back pain and even neck pain.

Rotational trunk shift (uneven shoulders and hips).

In some patients, years after the original surgery (particularly with the first generation of Harrington rods), the weight of the instrumentation can cause disk and joint degeneration severe enough to require surgery. Treatment may involve removal of the old instrumentation and extension of the fusion into the lower back.

Left untreated, or ineffectively treated, scoliosis carries long-term consequences.

Pain in adult-onset or untreated childhood scoliosis often develops because of posture problems that cause uneven stresses on the back, hips, shoulders, necks, and legs. Studies report, however, that patients with childhood scoliosis have the same incidence of back pain as the general population, which is very high (60% to 80%). In one study conducted 20 years after growth had stopped, two-thirds of adults who had lived with curvatures of 20 to 55 degrees reported back pain. In this study, most cases were mild, although other studies have reported that adults with a history of scoliosis tend to have chronic and more back pain than the general population.

Nearly all individuals with untreated scoliosis at some point develop spondylosis, an arthritic condition in the spine. The joints become inflamed, the cartilage that cushions the disks may thin, and bone spurs may develop. If the disk degenerates or the curvature progresses to the point that the spinal vertebrae begin pressing on the nerves, pain can be very severe and may require surgery. Even surgically treated patients are at risk for spondylosis if inflammation occurs in vertebrae around the fusion site.

The consequences of scoliosis are limited to the physical realm. The emotional impact of scoliosis, particularly on young girls or boys during their most vulnerable years, should not be underestimated. Adults who have had scoliosis and its treatments often recall significant social isolation and physical pain. Follow-up studies of children with scoliosis who did not have strong family and professional support often report significant behavioral problems.

Older people with a history of scoliosis, even those whose conditions were corrected, should realize that some negative emotional events in adulthood may possibly have their roots in their early experiences with scoliosis. Many studies have reported that patients who were treated for scoliosis have limited social activities and a poorer body image in adulthood. Some patients with a history of scoliosis have reported a slight negative effect on their sexual life. Pain appears to be only a minor reason for such limitation. An early Scandinavian study reported that adults with scoliosis had fewer job opportunities and a lower marriage rate than the general population.

It is clear, then, that scoliosis treatment options are presently lacking, and untreated scoliosis (except for mild to lower-moderate cases) is not an acceptable alternative.

There are many apparatus which are designed for attachment to, and positioning adjacent the spinal column, and in many instances, these apparatus are designed for use in treating spinal column anomalies, such as scoliosis. However, all known systems are limited by their design and known implementation modes on either arresting further deleterious rotation of the involved vertebrae, or fixing individual vertebrae once, by some means, they are brought to approximate a desired orientation and position.

Significant correction of severe scoliotic curvature to the point of approximating normal spinal configuration, particularly by a single process, is simply unknown in the art. This is, it is believed, the result of focus in the field on the positioning substantially seriatim of affected vertebrae. Applying derotational force to a vertebrae in this manner cannot effect en mass spinal reconfiguration without risking vertebral fracture at the point of spinal instrumentation fixation, particularly when using conventional instrumentation. Furthermore, significant, focused force applied to any individual vertebra risks spinal cord and related injury. Thus, only force which is inadequate to effect substantial correction to the entire spinal column is thus far ever applied, and correction of scoliotic curvatures are substantially limited.

It has become clear to the present inventor that desired levels of correction of spinal column anomalies, such as scoliosis, can only be achieved if the spinal column (or an affected segment thereof) is manipulated (or "derotated") substantially as a whole into a desired configuration. To achieve such an objective, force must be applied safely to all to-be-derotated vertebrae, and the forces necessary to reconfigure all, or at least a substantial portion of the spinal column must be dispersed throughout the affected spinal segments or regions. Nothing in the prior art satisfies these requirements, either individually or in combination.

SUMMARY OF THE INVENTION

In view of the foregoing, it is an object of the present invention to provide an improved system of spinal instrumentation for use in ameliorating aberrant spinal column deviation conditions, such as scoliosis.

It is another object of the present invention to provide an improved method for ameliorating aberrant spinal column deviation conditions, such as scoliosis.

It is another object of the present invention to provide an improved system of spinal instrumentation, and a method for the use thereof, for ameliorating aberrant spinal column deviation conditions, such as scoliosis, which system and method facilitates the application of significant derotational forces to individual vertebra, with substantially reduced risk for fracture thereof upon application of such forces.

It is another object of the present invention to provide an improved system of spinal instrumentation, and associated method for use thereof, in ameliorating aberrant spinal column deviation conditions, such as scoliosis, which system and method facilitates the application of forces to vertebrae of affected spinal column segments en bloc, thereby distributing otherwise potentially injurious forces in a manner for safely achieving over-all spinal column correction or derotation.

Applicant's present invention provides a system and method for use of such system which satisfy each of these objectives. Applicant's system includes bone screws which are to be implanted in the pedicle region(s) of individual to-be-derotated vertebrae. In the preferred mode of the present invention, such bone screws are also to be implanted in vertebrae to which balancing forces must be applied as the spinal column is manipulated en mass to achieve an over-all correction of the condition. The pedicle implantation provides a stable foundation for the application of significant derotational forces, but without undue risk of vertebral fracture.

The system includes a pedicle screw cluster derotation tool. This tool, in the presently preferred embodiment includes shafts, extending from a common handle or linked handle array, which are oriented and configured to extend to and engage the heads of a number of implanted pedicle screws which will have been implanted in adjacent vertebrae to which derotational or balancing forces are to be applied during a spinal column derotation and alignment. The engagement between the pedicle screw cluster derotation tool and the individual pedicle screws is such that, as manipulative forces are applied to the handle means of pedicle screw cluster derotation tool, forces are transferred and dispersed simultaneously among the engaged vertebrae. Therefore, a practitioner may, in a single motion, simultaneously and safely derotate multiple vertebrae of an affected spinal segment (as well as likewise apply balancing forces to other group(s) of vertebrae which are lateral to the effected segment(s).

The effect of practice of the present invention is three-dimensional correction which provides, not only spinal correction to near normal configuration, but corrects "rib humps."

The system of the present invention also includes, in its preferred embodiment, pedicle screws which allow for interfacing with, and fixation relative to pre-contoured spinal rods after a satisfactory derotation.

The present inventor's approach to the problems described above is certainly simple, when viewed in hindsight, but it is equally unobvious. In investigative procedures, the presently proposed system and method has achieved measure of correction of scoliotic curvature never before seen in orthopaedic practice.

BRIEF DESCRIPTION OF THE DRAWINGS

The present invention may be more easily understood with reference to figures, which are as follow:

FIG. 2 is an elevational dorsal view of the anatomical model of a human spinal column depicted in FIG. 1, but with an unobstructed view of already-implanted pedicle screws, and configured as if preceding the derotation step of the proposed method.

FIG. 3 is an elevational side view of the anatomical model of a human spinal column depicted in FIGS. 1 and 2, with an unobstructed view of already-implanted pedicle screws and with the pedicle screws through practice of the proposed method.

DETAILED DESCRIPTION OF THE PREFERRED EMBODIMENT

With reference to FIGS. 1-4 and 7, the spinal deviation correction system of the present invention includes a number of pedicle screws 10, each implanted in respective vertebrae to which rotative forces will be applied in a spinal anomaly correction.

Pedicle screws 10 may be of a variety of designs, such as, for example, are generally depicted in U.S. Pat. Nos. 6,743,237 (Gray, et al), 6,827,719 (Ralph, et al), 6,652,526 (Arafiles), 6,375,657 (Doubler, et al), the disclosures of which are incorporated herein by reference.

Figure 4:
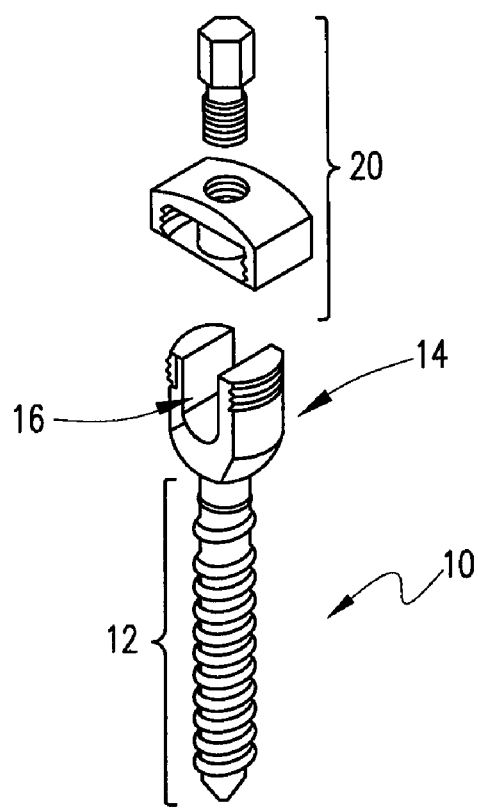
FIG. 4 is an example of a pedicle screw which may be used in the system of the present invention.

With particular reference to FIG. 4, pedicle screws 10 will include a threaded shank segment 12 and a head segment 14. Head segment will be configured with a spinal rod conduit (or channel) 16 or interfacing with a spinal rod 18 (shown in FIG.

3). Spinal rod engagement means 20 serve to fix pedicle screw 10 and spinal rod 18 in relative position and orientation, once a spinal column derotation is complete.

Figure 1:
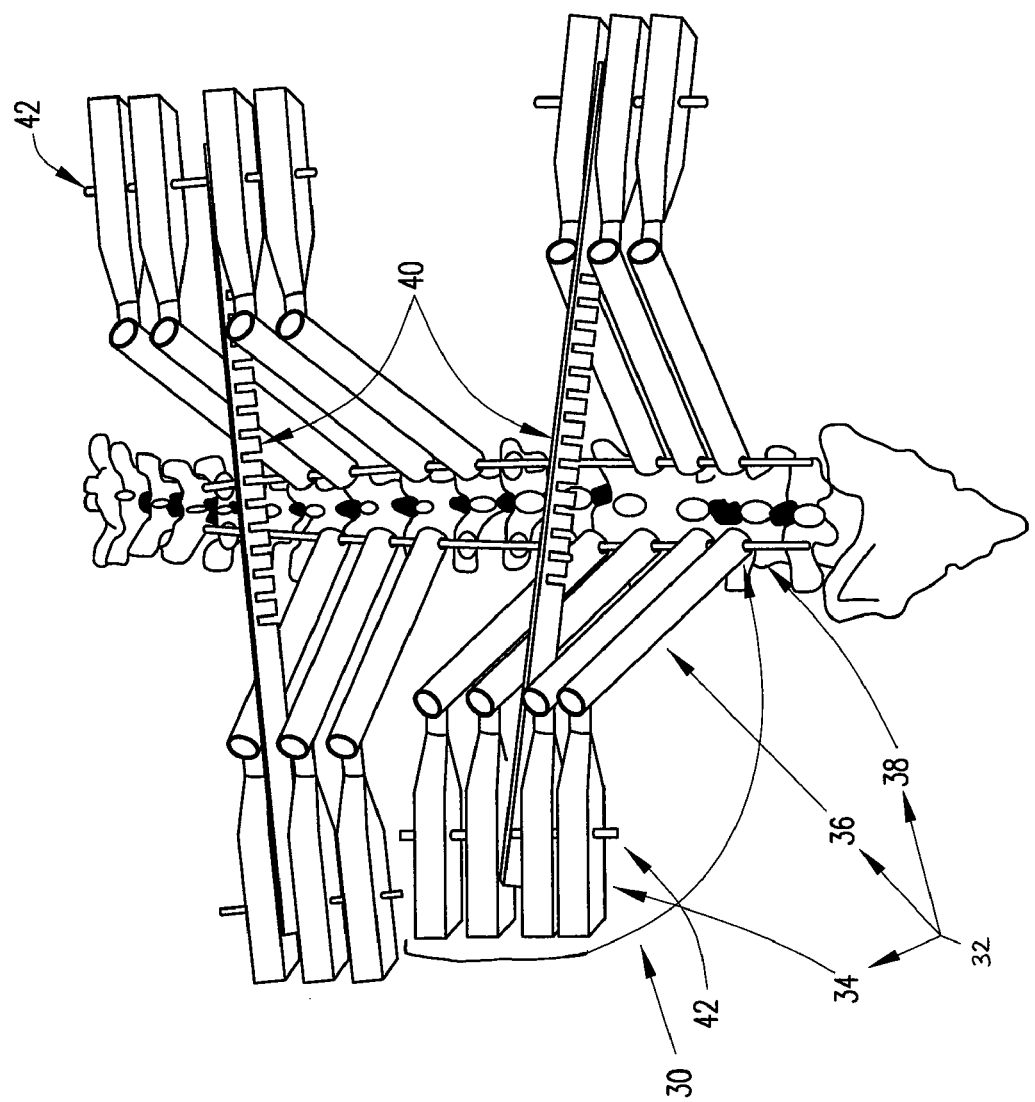
FIG. 1 is a top plan view of an anatomical model of a human spinal column, with components of the system of the present invention shown engaged therewith. The event depicted is that stage of the proposed method after which derotational and balancing forces have been applied to substantially correct a scoliotic curvature.

Referring again, generally to FIGS. 1-4, and 7, the system of the present invention further includes a pedicle screw cluster derotation tool 30. As depicted in FIG. 1, each pedicle screw cluster derotation tool 30 is configured from a grouping of pedicle screw wrenches 32, by a pedicle screw wrench linking member 42 joined together to act in unison during use.

Each pedicle screw wrench 32 includes a handle 34, a shaft 36, and a distal end 38 which is configured to reversibly engage the head segment 14 of a pedicle screw 10 such that, as shaft 36 is moved while shaft distal end 38 is engaged with head segment 14, manipulative forces are transferred to the pedicle screw 10 and, in turn, to the vertebra in which such pedicle screw 10 is implanted.

Significant variations of pedicle screw cluster derotation tool 30 are contemplated by the present invention. For example, the multiple wrenches 32, linked by wrench cross linking members 40, depicted in FIG. 1 may be replaced by a single handle member from which extend the functional equivalent of the multiple shafts 36 and shaft distal ends 38 for simultaneously engaging multiple pedicle screws 10, as depicted. However configured, the object and design of pedicle screw cluster derotation tool 30 is to facilitate simultaneous application of manipulative forces to multiple pedicle screws 10 which are implanted in a like number of vertebra. This has the effect of permitting the gross, en bloc application of sufficient derotative forces to affected segments of the spinal column in a sufficiently dispersed manner as to avoid injury to any one vertebra or isolated spinal column segment. This, in turn, facilitates a successful entire-spine, 3D derotation of a scoliosis patient to near normal parameters.

Figure 5:
FIG. 5 is a depiction of the complimentary forces applied to multiple spinal column segments to achieve an over-all spinal column correction.
Figure 7:
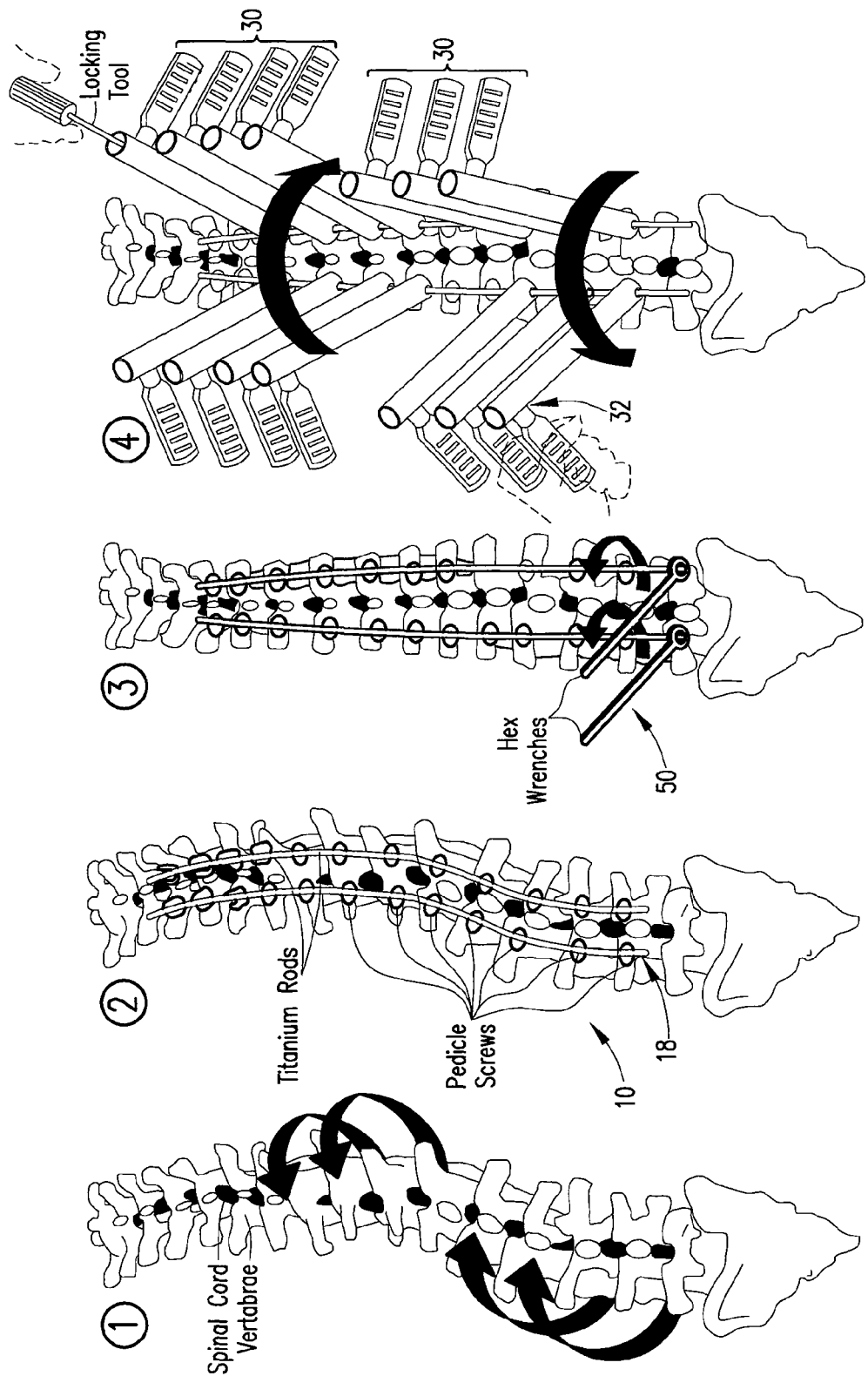
FIG. 7 is a 4-frame, progressive animation of the stages of correction of scoliosis according to the present method, with descriptive text included.

With reference to FIGS. 1-3, 5 and 7 the preferred mode of the present method usually involves application of forces to multiple spinal column segments, to achieve an over-all spinal column correction. For example, as depicted in FIGS. 5 and 7 in the case of a single curvature case of scoliosis, both derotative forces (illustrated by the central force vector arrow of FIG. 5) to vertebrae involved in scoliotic curvatures, as well as of balancing, or offsetting forces to lateral spinal segments (illustrated by the lateral arrows of FIG. 5) are applied.

The preferred mode of the present method involves pre-contouring spinal rods 18, as shown in FIG. 3 and frame 2 of FIG. 7. Such a contouring operation involves bending spinal rods 18 such that, in along two axes (analogous to yaw and pitch in aviation terms), the spinal rods 18 will substantially define, in one plane, a desired post-operative correction of the affected spinal column in reference to such two axes.

The spinal rod(s) 18 are loosely engaged with pedicle screws 10, and the pre-contoured spinal rod 18 are rotated from a first orientation, through approximately 90° to a second orientation, using hex wrenches 50 (see frame 3 of FIG. 7), to achieve a substantial correction of the scoliosis in the first two of three axes which will be corrected according to the present methodology, through use of the present system.

The next phase, after 2-D correction as just described, involves applying manipulative forces to pedicle screw clusters (in reference to a third axis (a "roll axis", again using aviation terms) using pedicle screw clusters derotation tool(s) 30 (see, inter alia, frame 4 of FIG. 7). After this final correction, spinal rod engagement means 20 is tightened to fix pedicle screw 10 and spinal rod 18 in relative position and orientation to secure the corrected spinal column configuration (now corrected with reference to all three relevant axes).

Spinal rod engagement means 20 of pedicle screws 10 are tightened, using an anti-torque feature of wrenches 32 (or of their equivalent in an alternative embodiment). This feature, as is well known in the art, allows tightening of nuts and the like, without imparting undue torque to the underlying apparatus or structure.

Figure 6:
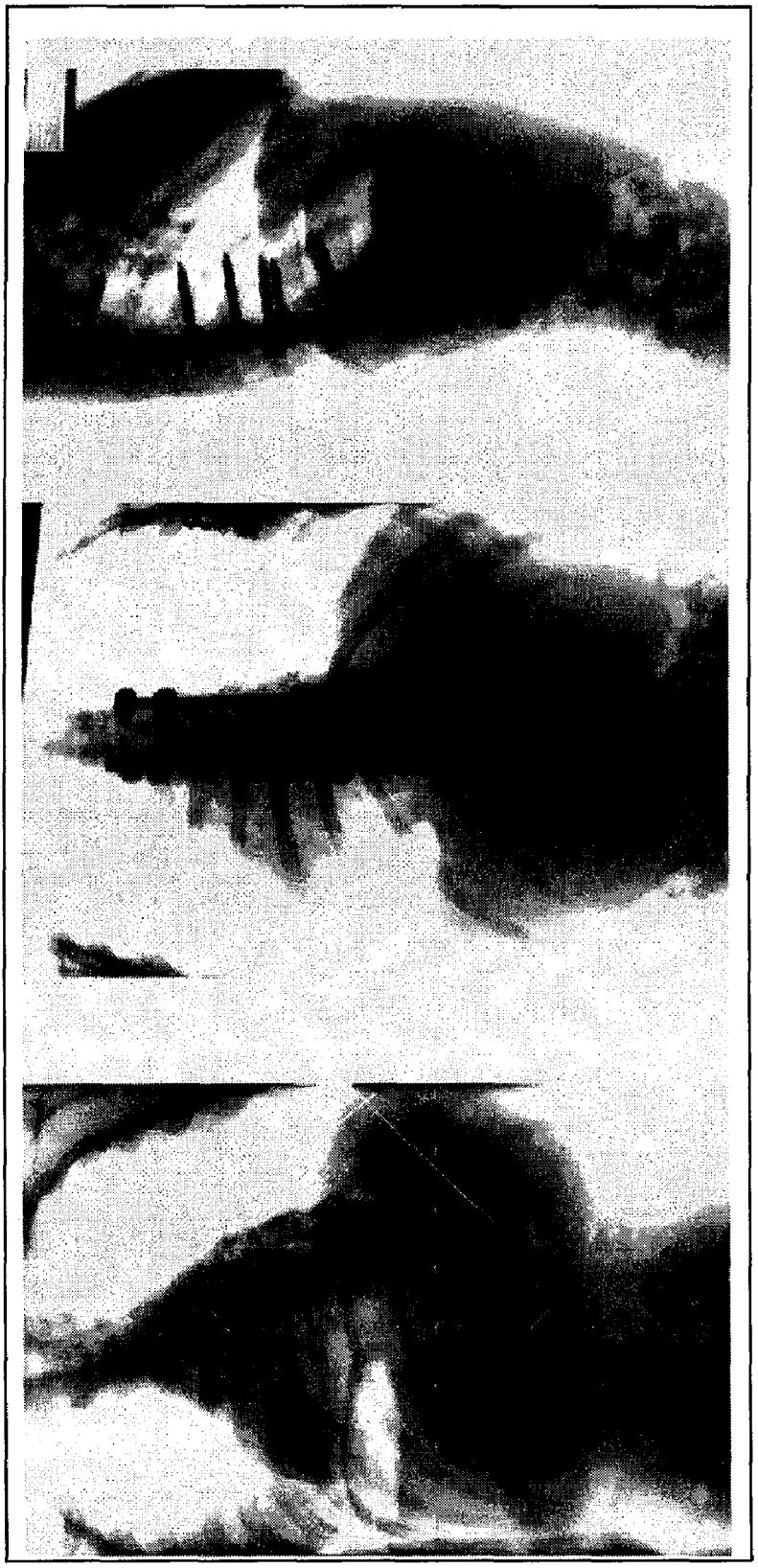
FIG. 6 is a three frame x-ray view showing "before and after" views of a scoliosis patient who was treated in an investigational procedure using the system and method of the present invention. The curvature correction was substantially to normal, and lumbar motion was preserved notwithstanding.

As shown in FIG. 6, investigative practice of the present method achieves efficacy never before seen in the orthopaedic field. The "before picture" is the left hand image of FIG. 6, and the two remaining images are sagittal and dorsal views of the corrected spinal column.

Although the invention has been described with reference to specific embodiments, this description is not meant to be construed in a limited sense. Various modifications of the disclosed embodiments, as well as alternative embodiments of the inventions will become apparent to persons skilled in the art upon reference to the description of the invention. It is, therefore, contemplated that the appended claims will cover such modifications that fall within the scope of the invention.

I claim:

1. A system for aligning vertebrae in the amelioration of aberrant spinal column deviation conditions comprising:
    a first set of pedicle screw, each pedicle screw having a threaded shank segment and a head segment; and
    a first pedicle screw cluster derotation tool, said first pedicle screw cluster derotation tool having a first handle means for facilitating simultaneous application of manipulative forces to said first set of pedicle screws and a first group of three or more pedicle screw engagement members which are mechanically linked with said first handle means, said first handle means configured to move simultaneously each pedicle screw engagement member; wherein each pedicle screw engagement member is configured to engage respectively with said head segment of each pedicle screw of said first set of pedicle screws; and wherein each pedicle screw engagement member is configured to transmit manipulative forces applied to said first handle means to said head segment of each pedicle screw of said first set of pedicle screws.

2. The system of claim 1 further comprising a spinal rod member, wherein one or more of said pedicle screws each includes:
    a spinal rod conduit formed substantially transverse of the length of each said pedicle screw and sized and shaped for receiving passage of said spinal rod member therethrough; and
    spinal rod engagement means for securing each said pedicle screw and said spinal rod, when extending through said spinal rod conduit, in a substantially fixed relative position and orientation.

3. A method for aligning vertebrae in the amelioration of aberrant spinal column deviation conditions comprising the steps of:
    selecting a first set of pedicle screws, each pedicle screw having a threaded shank segment and a head segment, each pedicle screw having a spinal rod engagement means for mechanically engaging with a spinal rod member and spinal rod fixation means for, upon actuation, fixing the relative orientation of each pairing of said spinal rod member and said pedicle screw;
    selecting a first pedicle screw cluster derotation tool, said first pedicle screw cluster derotation tool having a first handle means for facilitating simultaneous application of manipulative forces to said first set of pedicle screws and a first group of three or more pedicle screw engagement members which are mechanically linked with said first handle means, said first handle means moving each pedicle screw engagement member simultaneously, each pedicle screw engagement member being configured for engaging respectively with said head segment of each pedicle screw of said first set of pedicle screws, and transmitting manipulative forces applied to said first handle means to said head segment of each pedicle screw of said first set of pedicle screws;

implanting each pedicle screw of said first set of pedicle screws in a pedicle region of each of a first group of vertebrae of a spinal column which exhibits an aberrant spinal column deviation condition;

contouring said spinal rod member whereby, in a first plane, said spinal rod member substantially defines, in reference to two axes, a post-operative spinal column alignment for said spinal column;

engaging said spinal rod respectively with said spinal rod engagement means of each pedicle screw of said first set of pedicle screws, while said spinal rod is in a first rotational orientation;

rotating said spinal rod substantially along its length to a second rotational orientation to effect a correction of spinal column deviation in reference to two axes;

engaging each pedicle screw engagement member of said first group of pedicle screw engagement members respectively with said head segment of each pedicle screw of said first set of pedicle screws; and applying manipulative force to said first handle means in a manner for simultaneously engaging said first group of three or more pedicle screw engagement members and said first set of pedicle screws and thereby in a single motion simultaneously rotating said vertebrae of said first group of vertebrae in which said pedicle screws are implanted to achieve an amelioration of an aberrant spinal column deviation condition in reference to a third axis.

4. The method of claim 3 further comprising the steps of:

selecting a second set of pedicle screws;

selecting a second spinal rod member;

selecting a second pedicle screw cluster derotation tool, said second pedicle screw cluster derotation tool having a second handle means for facilitating simultaneous application of manipulative forces to said second set of pedicle screws and a second group of pedicle screw engagement members which are mechanically linked with said second handle means, said second handle means moving each pedicle screw engagement member simultaneously, each pedicle screw engagement member being configured for engaging respectively with said head segment of each pedicle screw of said second set of pedicle screws, and transmitting manipulative forces applied to said second handle means to said head segment of each pedicle screw of said second set of pedicle screws;

implanting each pedicle screw of said second set of pedicle screws in the pedicle region of each of a second group of vertebrae of a spinal column which exhibits an aberrant spinal column deviation condition;

contouring said second spinal rod member whereby, in a first plane, said second spinal rod member substantially defines, in reference to two axes, a post-operative spinal column alignment for said spinal column;

engaging said second spinal rod respectively with said spinal rod engagement means of each pedicle screw of said second set of pedicle screws, while said second spinal rod is in a first rotational orientation;

rotating said second spinal rod substantially along its length to a second rotational orientation to effect a correction of spinal column deviation in reference to two axes;

engaging each pedicle screw engagement member of said second group of pedicle screw engagement members respectively with said head segment of each pedicle screw of said second set of pedicle screws; and applying manipulative force to said second handle means in a manner for simultaneously engaging said second group of pedicle screw engagement members and said second set of pedicle screws and thereby in a single motion simultaneously rotating said vertebrae of said second group of vertebrae in which said pedicle screws are implanted to achieve an amelioration of an aberrant spinal column deviation condition.

* * * * *